(12) United States Patent
Perricone

(10) Patent No.: US 6,319,942 B1
(45) Date of Patent: Nov. 20, 2001

(54) TOPICAL SCAR TREATMENTS USING ALKANOLAMINES

(76) Inventor: Nicholas V. Perricone, 27 Coginchaug Ct., Guilford, CT (US) 06437

( * ) Notice: Subject to any disclaimer, the term of this patent is extended or adjusted under 35 U.S.C. 154(b) by 0 days.

(21) Appl. No.: 09/875,317

(22) Filed: Jun. 6, 2001

(51) Int. Cl.[7] ...................... A61K 31/385; A61K 31/195; A61K 31/13
(52) U.S. Cl. ......................... 514/440; 514/561; 514/667
(58) Field of Search ..................................... 514/440, 561, 514/667

(56) References Cited

U.S. PATENT DOCUMENTS 5,945,102 * 8/1999 De Faire et al. ................. 424/94.63
6,203,793 * 3/2001 Lipsky et al. ..................... 424/143.1

* cited by examiner

*Primary Examiner*—Raymond Henley, III
(74) *Attorney, Agent, or Firm*—Mary M. Krinsky

(57) ABSTRACT

Cutaneous scars are reduced by the topical application of compositions containing an alkanolamine such as ethylaminoethanol, methylaminoethanol, dimethylaminoethanol, isopropanolamine, triethanolamine, isopropanoldimethylamine, ethylethanolamine, 2-butanolamine, choline, serine, and mixtures thereof. Compositions may be applied directly to scar tissue, or embedded in linaments held against the scars. Dimethylaminoethanol in amounts ranging from about 0.1% to about 10% by weight of the total composition is particularly preferred. Adjunct ingredients such as lipoic acid, tyrosine, ascorbyl palmitate, and glycolic acid may be added to scar-reducing formulations, and are desirable in many embodiments.

20 Claims, No Drawings

TOPICAL SCAR TREATMENTS USING ALKANOLAMINES

BACKGROUND OF THE INVENTION

1. Field of the Invention

This invention relates primarily to methods and compositions for the treatment of scar tissue, particularly hypertrophic and keloid scars and straie distensae (stretch marks). Scars typically result from repair of damaged tissue, and this damage may be following trauma, burns, or disease. Because scars are cosmetically distracting and sometimes symptomatic, producing bothersome itching, burning, stinging or painful sensations, there is considerable interest in their treatment.

2. Description of Related Art

Scars result from wound healing, which occurs in three separate phases: inflammation, formation of granulation tissue, and matrix formation. (For a review, see Sahl, W. J., and Clever, H., *Internat. J. Derm.*, 1994, 33: 681–691 (part I) and 763–769 (part II); this paper, and others and patents cited below are expressly incorporated herein in their entireties by reference). During the first phase, damage to endothelial cells, complement, and platelets at the wound site release chemotactic factors that result in the infusion of neutrophils, lymphocytes and macrophages, which aids in the removal of infection and foreign debris. As in all inflammatory processes, there is generation of free radicals, which damages cell membranes and results in formation of oxidized proteins and fats, and cross-linked new collagen, laying a scaffold for the next phase.

At the end of the inflammatory phase, the granulation phase begins with an influx of fibroblasts and endothelial cells to the wound. Other key cells in this phase are macrophages and platelets. Macrophages induce the beginning of granulation by relasing platelet-derived growth factor (PDGF), tumor necrosis growth factor (TGF)-$\alpha$, and an epidermal growth factor-like substance. Activated platelets release epidermal growth factor (EGF), PDGF, TGF-$\alpha$, and TGF-$\beta$. Together these play roles in the re-epithelialization process wherein keratinocytes cells migrate in sheaths over a provisional matrix consisting primarily of fibrin, fibronectin, type V collagen, and tenascin, and produce their own fibronectin receptors.

Once re-epithelilization has occurred, keratinocytes resume their normal differentiated form, and matrix formation begins. Matrix formation consists primarily of the construction of derma matrix, which is regulated by fibroblasts. Chemotaxis of fibroblasts results in the production of abundant quantities of hyaluronate, fibronectin, and types I and III collagen. These components comprise the bulk of the provisional extracellular matrix in the early part of this wound repair phase. Hyaluronic acid (HA) creates an open-weave pattern in the collagen/fibronectin scaffold, facilitating fibroblast movement. HA production falls after about the fifth day of wound healing, and levels of chronroitin sulfate in dermatan sulfate increase. Fibronectin deposits in the collagen, and wound contraction begins. Biochemically during the contraction stage, hyaluronidase and proteinase are present, type I collagen synthesis is stimulated, and increased levels of chronroitin sulfate, dermatin sulfate and proteoglycans are observed; together these restructure the matrix. At the end of the healing process, the final scar shows collagen fibers mostly parallel to the epidermis.

Hypertrophic and keloid-type scars result in extension of scar tissue so that a bulky lesion results. A keloid is an exuberant scar that proliferates beyond the original wound. It should be noted that keloids only occur in humans, often causing burning, stinging and itching sensations as well as cosmetic embarrassment. The etiology of unsightly keloid formation is not known. However, in keloids, fibronectin formation continues for years, while fibronectin formation in normal scars disappears within a few days after wound closure. Keloid scars exhibit a high rate of collage synthesis in comparison to normal scars, and a low proportion of cross-linked collagen.

Hypertrophic scars sometimes are difficult to distinguish from keloid scars histologically and biochemically, but unlike keloids, hypertropic scars remain confined to the injury site and often mature and flatten out over time. Both types secrete larger amounts of collagen than normal scars, but typically the hypertrophic type exhibits declining collagen synthesis after about six months. However, hypertrophic scars contain nearly twice as much glycosaminoglycan as normal scars, and this and enhanced synthetic and enzymatic activity result in significant alterations in the matrix which affects the mechanical properties of the scars, including decreased extensibility that makes them feel firm.

Atrophic scars are characterized by a thinning and diminished elasticity of the skin due to a loss of normal skin architecture. An example of an atrophic scar is striae distensae, also known as stretch marks. Striae commonly occur in postpartum women after childbirth and also during times of larger-than-average weight gain and also in association with steroids. Atrophic scars are sometimes also observed after trauma, infection and disease, and may show loss of surface markings and smoothness or dry, from wrinkles over time.

Formation of scars, especially hypertrophoic and keloid scars, is dependent on systemic growth factors such as interleukins and other cytokines, and their influence on fibronectin and collagen biosynthesis. Cytokines are released and are present in the wound healing process and sometimes are released in the inflammatory stage. Growth factors and other cytokines vary in the inflammatory stage and are released based, among other complex interactions, upon the redox state of the cells. The presence of free radicals in the inflammatory stage plays an important factor in wound healing. Factors that increase the presence of free radicals, such as infection, radiation, and continued trauma, may instigate hypertrophic and keloid scar formation. It is important to note that cytokines have been suggested to regulate nitric oxide synthetase, which controls the formation of nictric oxide, which plays an important role in signal transduction in the cells. It is also known that nitric oxide synthetase activity is aberrant in keloid scars when compared to normal tissue (Lim, T. C., et al., *Plastic and Reconst. Surgery*, 1996, 98: 911–912). Hypertrophic and keloid scars also show inflammatory activity that is not seen in mature scars.

Many scar treatments have been suggested, but few are satisfactory. Treatment of keloid or hypertrophic scars have consisted of surgical excision followed by graft application. Pressure has also been used to cause scar thinning; for example, pressure bandages placed over scars have resulted in some scar thinning, but a pressure of at least about 25 mm Hg must be maintained constantly for approximately six months in usual situations for any visually observable effect. Ionizing radiation therapy has also been employed. Other treatments include application of silicone pads to the scar tissue surface, sometimes under pressure provided by an elastomeric bandage, topical application of silicone gel sheets, with or without added vitamin E (Palmieri, B., et al., *J. Derm.*, 1995, 34: 506–509), and topical or intralesional treatment with corticosteroids.

Scars are one of the strongest forces driving the cosmetic industry. It would be desirable to have alternative, preferably new and improved, treatments for scar reduction and remodeling.

BRIEF SUMMARY OF THE INVENTION

It is an objective of this invention to provide compositions and methods for the treatment and inhibition of scar tissue, including hypertrophic, keloid, and atrophic scars.

It is another and more specific objective of the invention to provide topical compositions and simple methods for scar reduction and inhibition based upon direct topical application of compositions containing active ingredients and/or linaments such as a silicone gel sheet embedded with active ingredients, to scars and to injured skin sites susceptible to scarring.

These and other objectives are accomplished by the present invention, which provides compositions and methods for the treatment and/or inhibition of cutaneous scars, which comprises topical application to the scars or injured skin areas of an effective amount of an alkanolamine such as ethylaminoethanol, methylaminoethanol, dimethylaminoethanol, isopropanolamine, triethanolamine, isopropanoldimethylamine, ethylethanolamine, 2-butanolamine, choline, serine, and mixtures thereof. Dimethylaminoethanol is particularly preferred. Amounts of active alkanolamine ingredient in scar-reducing topical compositions of the invention range from about 0.1% to about 10%, more narrowly from about 1% to about 3%, by weight of the total composition. Adjunct ingredients such as lipoic acid, tyrosine, a fatty acid ester of ascorbic acid, e.g., ascorbyl palmitate, and/or an α-hydroxy acid, e.g., glycolic acid may be added to scar-reducing formulations of the invention. One particularly efficacious embodiment for scars employs a composition containing diethylaminoethanol, lipoic acid, and tyrosine; the composition may, optionally, contain other ingredients. Methods and compositions of the invention are particularly efficacious for acne scars and stretch marks.

BRIEF SUMMARY OF THE INVENTION

Methods of the invention involve the topical administration of dimethylaminoethanol and/or other structurally related alkanolamines, or their biologically equivalent derivatives, to mammalian skin scars for the reduction and inhibition of epidermal and subepidermal cutaneous scar tissue, including underlying membrane and connective tissue typically damaged in various types of skin trauma. Active alkanolamine active ingredients may be applied alone, or in combination with other ingredients such as lipoic acid and/or tyrosine to enhance the efficacy of the scar treatment.

In the practice of the invention, compositions containing an effective amount of an alkanolamine of the formula

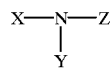

wherein X, Y and Z are selected from the group consisting of hydrogen, $C_1$–$C_3$ alkyl groups, $C_2$–$C_4$ alkanol group, wherein at least one of X, Y, or Z is a $C_2$–$C_4$ alkanol group bearing at least one hydroxyl group and optionally at least one carboxyl group, are applied to mammalian skin to reduce or inhibit scars. Useful compounds for the invention include, but are not limited to, ethylaminoethanol, methylaminoethanol, dimethylaminoethanol, isopropanolamine, triethanolamine, isopropanoldimethylamine, ethylethanolamine, 2-butanolamine, choline, serine, and mixtures thereof. Many preferred embodiments employ methylaminoaminoethanol, dimethylaminoethanol, ethylaminoethanol, and/or triethanolamine; particularly preferred is dimethylaminoethanol, (DMAE).

However, only effective amounts of alkanolamines are needed to reduce scars, so generally topical application is accomplished in association with a carrier, and particularly one in which the alkanolamine active ingredient is soluble per se or is effectively solubilized (e.g., as an emulsion or microemulsion). Where employed, the carrier is inert in the sense of not bringing about a deactivation or oxidation of the polyphenol, and in the sense of not bringing about any adverse effect on the skin areas to which it is applied. In one preferred practice of the invention, dimethylaminoethanol is applied in admixture with a dermatologically acceptable carrier or vehicle (e.g., as a lotion, cream, ointment, soap, stick, or the like) so as to facilitate topical application and, in some cases, provide additional therapeutic effects as might be brought about, e.g., by moisturizing of the affected skin areas. While the alkanolamine carrier for dermatological compositions can consist of a relatively simple solvent or dispersant such as water, it is generally preferred that the carrier comprise a composition more conducive to topical application, and particularly one which will form a film or layer on the skin to which it is applied so as to localize the application and provide some resistance to washing off by immersion in water or by perspiration and/or aid in the percutaneous delivery of the active agent. Many preparations are known in the art, and include lotions containing oils and/or alcohols and emollients vegetable oils, hydrocarbon oils and waxes, silicone oils, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. One preferred embodiment is an oil-in-water cream. Such compositions are referred to herein as dermally or dermatologically acceptable carriers, and are formulated using conventional techniques known to those of ordinary skill in the art.

Suitable carriers include water, alcohols, oils and the like, chosen for their ability to dissolve or disperse polyphenol and any other ingredients used in the treatment. Generally, even low concentrations of active ingredient in a carrier are suitable, depending upon the application regimen and adjunct ingredients employed. Many embodiments contain from about 0.1% to about 10% by weight, more narrowly from about 0.25% to about 5% to 7% by weight, and in many cases from about 1% to about 3% by weight, alkanolamine such as dimethylaminoethanol in the total composition. Pronounced scar tissue may require more frequent treatments with compositions having higher concentrations of alkanolamines, or silicone gel sheets or other linaments embedded with alkanolamines discussed below. As a practical matter, however, to avoid the need for repeated application, it is desirable that the topically applied composition (i.e., alkanolamine plus carrier) be formulated to contain at least about 1% by weight alkanolamine, and many embodiments contain more than 1 weight % alkanolamine. One efficacious embodiment contains from about 2% to about 5% by weight alkanolamine.

Generally in the practice of methods of the invention, the scar-reducing composition is topically applied to the affected skin areas in a predetermined or as-needed regimen either at intervals by application of a lotion or the like, it generally being the case that gradual improvement is noted with each successive application. Insofar as has been determined based upon clinical studies to date, no adverse side effects are encountered.

Alternative embodiments employ a silicone gel sheet or other linament to which alkanolamines of the invention such as dimethylaminoethanol have been added. These may be pressure or adhesive bandages. Silicone gel sheets useful in the practice of the invention are typically cross-linked polydimethylsiloxane containing or impregnated with alkanolamine. It is an advantage of the invention that DMAE and other active alkanolamines augment the effectiveness of previously disclosed methods of using lipoic acid and/or silicone pads or gel sheets for diminishing scars (see U.S. Pat. No. 5,965,618 to Perricone and Palmieri, et al., cited above).

Whether they are topical compositions directly applied to scar tissue or linaments embedded with alkanolamine active ingredients, some embodiments of this invention contain at least one other adjunct ingredient in addition to alkanolamine. Adjunct ingredients include, but are not limited to, lipoic acid, α-hydroxy acids, tyrosine, and fatty acid esters of ascorbic acid. Many embodiments employ more than one adjunct ingredient. Where employed, adjunct ingredients are anticipated to have additive effects if not synergistic effects due to different mechanisms of action.

A particularly preferred adjunct ingredient is lipoic acid. As described in 1999 by Perricone (U.S. Pat. No. 5,965, 618), scar tissue is reduced or inhibited by application of lipoic acid compositions to scarred skin tissue. Compositions of the invention containing both alkanolamine and lipoic acid are also efficacious in treating scars. As used herein, the term "lipoic acid" encompasses thioctic acid (1,2-dithiolane-3-pentanoic acid; 1,2-dithiolane-3-valeric acid), $C_8H_{14}O_2S_2$, formula weight 206.32, and biologically equivalent lipoic acid derivatives, including dihydrolipoic acid. Lipoic acid was originally identified as a bacterial growth factor present in the water-soluble fraction of liver and yeast. It was found to be necessary for the oxidative decarboxylation of pyruvic acid by *Streptococcus fecalis* and for the growth of *Tetrahymena gelii*, and replaced acetate for the growth of *Lactobacillus casei*. It has been variously known as acetate replacing factor, protogen A, and pyruvate oxidation factor.

Lipoic acid derivatives include thioctic acid esters, particularly alkyl esters such as fatty acid esters, amides, particularly those isolated from or mimicking naturally occurring lipoamides, salts, particularly alkali metal salts, anhydrides and specifically includes the reduced form, dihydrolipoic acid and its esters, amides and salts. Since lipoic acid is both fat- and water-soluble, it is an advantage of the invention that it can be used in either lipid or aqueous-based compositions, and it readily crosses cellular membranes and disperses in extracellular and intracellular tissue components. Derivatives may also include those involving other reactive groups known to those skilled in the art. As used herein, the term "derivatives" includes metabolic precursors of lipoic acid. Where lipoic acid derivatives are employed, they must be functionally equivalent to lipoic acid.

In typical embodiments of the invention containing lipoic acid as an adjunct ingredient, the composition contains from about 0.1% to about 7 weight %, lipoic acid or dihydrolipoic acid. In one embodiment, about 2% to 3% lipoic acid is employed with the alkanolamine active ingredient.

As used herein, the term "α-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Preferred α-hydroxy acids and/or α-hydroxy acid derivatives are less bulky structurally so that they penetrate the skin well, and thus have a backbone of from one to three carbon atoms such as those set out in U.S. Pat. No. 5,965,618 at column 6 lines 4 to 29. Where employed, glycolic and/or lactic acid or their derivatives are preferred; glycolic acid is especially efficacious. Glycolic acid or other α-hydroxy acid is typically present in amounts ranging from about 1% to about 10%, more narrowly from about 3% to about 7% of the total composition.

Tyrosine may be present in scar-reducing compositions of the invention in amounts typically from about 0.01% to about 5%, more preferably from about 0.04% to about 3% by weight, and most preferably about 0.5% by weight, based on the total composition.

Fat-soluble fatty acid esters of ascorbic acid (vitamin C) is employed as an adjunct ingredient in other embodiments, alone or in combination with α-hydroxy acids. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate. It is an advantage of the invention that where fatty acid esters of ascorbic acid are employed as an adjunct ingredient, they help stabilize the alkanolamine in the composition. Ascorbyl palmitate and the like ascorbyl esters are typically present in amounts ranging from about 0.5% to about 15%, preferably from about 1% to about 7% to 10%, of the total composition.

Scar-reducing topical compositions of the invention can comprise additional ingredients commonly found in skin care compositions, such as, for example, emollients, skin conditioning agents, emulsifying agents, humectants, preservatives, antioxidants, perfumes, chelating agents, etc., provided that they are physically and chemically compatible with other components of the composition. Preservatives include, but are not limited to, $C_1$–$C_3$ alkyl parabens and phenoxyenthanol, typically present in an amount ranging from about 0.5% to about 2.0% by weight percent, based on the total composition. Emollients, typically present in amounts ranging from about 0.01% to 5% of the total composition include, but are not limited to, fatty esters, fatty alcohols, mineral oils, polyether siloxane copolymers, and mixtures thereof. Humectants, typically present in amounts ranging from about 0.1% to about 5% by weight of the total composition include, but are not limited to, polyhydric alcohols such as glycerol, polyalkylene glycols (e.g., butylene glycol, propylene glycol, dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, and mixtures thereof. Emulsifiers, typically present in amounts from about 1% to about 10% by weight of the composition, include, but are not limited to, stearic acid, cetyl alcohol, stearyl alcohol, steareth 2, steareth 20, acrylates/$C_{10-30}$ alkyl acrylate crosspolymers, and mixtures thereof. Chelating agents, typically present in amounts ranging from about 0.01% to about 2% by weight, include, but are not limited to, ethylenediamine tetraacetic acid (EDTA) and derivatives and salts thereof, dihydroxyethyl glycine, tartaric acid, and mixtures thereof. Antioxidants, typically present in an amount ranging from about 0.02% to about 0.5% by weight of the composition, include, but are not limited to, butylated hydroxy toluene (BHT); vitamin C and/or vitamin C derivatives, such as fatty acid esters of ascorbic acid, particularly asocorbyl palmitate; butylated hydroanisole (BHA); phenyl-α-naphthylamine; hydroquinone; propyl gallate; nordihydroquiaretic acid; vitamin E and/or derivatives of vitamin E, including tocotrienol and/or tocotrienol derivatives; calcium pantothenates; green tea extracts; mixed polyphenols; and mixtures of any of these. As mentioned above, particularly preferred antioxidants are those that provide additional benefits to the skin such as ascorbyl palmitate and tocotrienol, and formulations using tocotrienol-enriched oils. (See additional ingredients and methods in U.S. Pat. Nos. 4,775,530, 5,376,361, 5,409,693, 5,545,398, 5,574,063, 5,643,586, 5,709,868, 5,879,690, 5,965,618, 5,968,618, 6,051,244, 6,142,419, and 6,191,121 to Perricone).

Buffering agents are employed in many compositions. Preferably, the amount of buffering agent is one that results in compositions having a pH ranging from about 4.5 to about 8.5, more preferably from about 5.5 to about 8.5, most preferably from about 6.5 to about 8.0. Typical buffering agents are chemically and physically stable agents commonly found in cosmetics, and can include compounds that are also adjunct ingredients such as citric acid, malic acid, and glycolic acid buffers.

Typical compositions of the invention comprise diethylaminoethanol alone; diethylaminoethanol and lipoic acid; a combination of diethylaminoethanol, lipoic acid, and tyrosine; and a combination of diethylaminoethanol, lipoic acid, tyrosine, and glycolic acid. Embodiments employing the occlusive effects of silicone pads or gel sheets to diminish scars generally employ higher concentrations of alkanolamine active ingredients and adjunct ingredients to provide maximal efficacy. A preferred embodiment used in a double blind, placebo-controlled study was a composition containing 3% by weight dimethylaminoethanol, 5% tyrosine, 3% lipoic acid, and 7% glycolic acid.

While not wishing to be bound to any theory, it is possible that diethanolamine, alone or in combination with adjunct ingredients such as lipoic acid, is efficacious in the treatment of scar tissue because it acts as a free radical scavenger and neutralizer, and prevents the cross-linking of cell membranes that is seen in scar formation, particularly keloid scar formation. By the same token, alkanolamine modulation of free radicals and other oxidative species involved in the activation of proinflammatory and inflammatory cascades that cause the formation of toxic intermediates and end products, resulting in further, continuous, and ultimately greater damage than that caused by the initial transient reactive species. Transcription factors such as NFκB and AP1 are activated in inflammation, which in turn cause production of proinflammation mediators. These mediators, such as TFα and various interleukins, cause a burst of cytokines. Arachadonic acid is released, which is itself toxic, and it is oxidized to biologically active mediators. When arachadonic acid is oxidized via the cyclooxygenase or lipoxygenase pathways, for example, prostaglandins, leukotrines, and hyroxyeicosatetraenoic acid (HETE) are produced, which cause erythema, edema, and additional free radical production accelerating the process. These and other undesirable metabolites permeate and disrupt cell membranes, mitochondrial membranes, and nuclear membranes. Compositions of the invention appear to help to reverse this incessant membrane damage, including the deleterious cross-linkage and/or cleavage of proteins and lipoproteins and oxidation of membrane lipids and lipoproteins observed in the formation of scar tissue, largely by by stabilizing membranes and stimulating the formation of healthy collagen over damaged collagen. Alkanolamines, alone or in combination with adjunct ingredients such as lipoic acid and tyrosine, apparently stimulate the activation of transcription factors that results in production of metalloproteinases that seem to remodel damaged collagen, which results in desirable effects.

The method of the present invention is particularly useful for reducing or inhibiting scars caused by minor lacerations, surgical wounds, vaccines, burns, and abrasions, as well as stretch marks observed in aging and after weight loss or childbirth and various types of fibroses. Generally, the composition is topically applied to the affected skin areas in a predetermined or as-needed regimen either at intervals by application of a lotion or the like, or continuously using a silicone gel sheet, it generally being the case that gradual improvement is noted with each successive application. Insofar as has been determined based upon clinical studies to date, no adverse side effects are encountered.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for the treatment or inhibition of cutaneous scar tissue comprising applying to said tissue a composition containing an effective amount of an alkanolamine of the formula

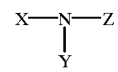

wherein X, Y and Z are selected from the group consisting of hydrogen, $C_1$–$C_3$ alkyl groups, $C_2$–$C_4$ alkanol group, wherein at least one of X, Y, or Z is a $C_2$–$C_4$ alkanol group bearing at least one hydroxyl group and optionally at least one carboxyl group.

2. A method according to claim 1 wherein the alkanolamine is selected from the group consisting of ethylaminoethanol, methylaminoethanol, dimethylaminoethanol, isopropanolamine, triethanolamine, isopropanoldimethylamine, ethylethanolamine, 2-butanolamine, choline, serine, and mixtures thereof.

3. A method according to claim 2 wherein the alkanolamine is dimethylaminoethanol.

4. A method according to claim 1 wherein the alkanolamine is present in the composition in an amount ranging from about 0.1% to about 10% by weight of the composition.

5. A method according to claim 4 wherein the alkanolamine is present in the composition in an amount ranging from about 1% to about 3% by weight of the composition.

6. A method according to claim 1 wherein the composition further comprises at least one adjunct ingredient selected from the group consisting of lipoic acid, tyrosine, an α-hydroxy acid, a fatty acid ester of ascorbic acid, and mixtures of any of these.

7. A method according to claim 6 wherein the composition comprises lipoic acid.

8. A method according to claim 6 wherein the composition comprises tyrosine.

9. A method according to claim 6 wherein the composition comprises glycolic acid.

10. A method according to claim 6 wherein the composition comprises ascorbyl palmitate.

11. A method according to claim 6 wherein the composition comprises lipoic acid and tyrosine.

12. A method according to claim 1 wherein the composition further comprises another ingredient selected from the group consisting of a preservative, an emollient, an antioxidant, an emulsifier, a humectant, a buffer, and mixtures of any of these.

13. A method according to claim 1 wherein silicone gel sheets impregnated with the composition are applied to the scar tissue.

14. A method for the treatment or inhibition of cutaneous scar tissue comprising applying to said tissue a composition containing from about 0.1% to about 10% by weight of an alkanolamine selected from the group consisting of ethylaminoethanol, methylaminoethanol, dimethylaminoethanol, isopropanolamine, triethanolamine, isopropanoldimethylamine, ethylethanolamine, 2-butanolamine, choline, serine, and mixtures thereof.

15. A method according to claim 14 wherein the composition comprises dimethylaminoethanol.

16. A method according to claim 14 wherein the composition comprises from about 1% to about 3% by weight alkanolamine.

17. A method according to claim 14 wherein the composition further comprises at least one adjunct ingredient selected from the group consisting of lipoic acid, tyrosine, glycolic acid, ascorbyl palmitate, and mixtures of any of these.

18. A method according to claim 14 which reduces acne scars.

19. A method for reducing cutaneous scar tissue comprising applying to said tissue a linament embedded with an effective amount of dimethylaminoethanol.

20. A method according to claim 19 wherein the linament is embedded with a composition containing from about 0.1% to about 10% dimethylaminoethanol and at least one other ingredient selected from the group consisting of from about 0.1% to about 7% by weight lipoic acid, from about 0.1% to about 5% by weight tyrosine, from about 1% to about 10% by weight of glycolic acid, from about 0.5% to about 15% by weight ascorbyl palmitate, and mixtures of any of these.

* * * * *